US010296754B2

(12) United States Patent
Son et al.

(10) Patent No.: US 10,296,754 B2
(45) Date of Patent: May 21, 2019

(54) METHOD FOR CONTROLLING SECURITY SYSTEM AND ELECTRONIC DEVICE THEREOF

(71) Applicant: Samsung Electronics Co., Ltd., Gyeonggi-do (KR)

(72) Inventors: Dong-Il Son, Gyeonggi-do (KR); Heung-Sik Shin, Jeollabuk-do (KR); Eui-Chang Jung, Seoul (KR); Ju-Yeong Lee, Seoul (KR); Ki-Tae Lee, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 13 days.

(21) Appl. No.: 14/975,176

(22) Filed: Dec. 18, 2015

(65) Prior Publication Data
US 2016/0104006 A1    Apr. 14, 2016

Related U.S. Application Data

(63) Continuation of application No. 14/528,744, filed on Oct. 30, 2014, now Pat. No. 9,652,626.

(30) Foreign Application Priority Data

Oct. 30, 2013  (KR) .................. 10-2013-0130471

(51) Int. Cl.
*G06F 21/00*    (2013.01)
*G06F 21/62*    (2013.01)
(Continued)

(52) U.S. Cl.
CPC ...... *G06F 21/6218* (2013.01); *A61B 5/02438* (2013.01); *A61B 5/681* (2013.01);
(Continued)

(58) Field of Classification Search
CPC ........ G06F 1/163; A61B 5/681; H04W 4/008; H04W 12/06
See application file for complete search history.

(56) References Cited

U.S. PATENT DOCUMENTS 7,257,374 B1    8/2007  Creigh
8,725,842 B1 *  5/2014  Al-Nasser ............ G04G 17/08
                                              367/11
(Continued)

FOREIGN PATENT DOCUMENTS

KR    2020000031506    11/2000
KR    1020057001651     8/2005
(Continued)

OTHER PUBLICATIONS

U.S. Office Action dated Jul. 14, 2016 issued in counterpart U.S. Appl. No. 14/528,744, 23 pages, Nov. 28, 2016.

*Primary Examiner* — Alexander Lagor
(74) *Attorney, Agent, or Firm* — The Farrell Law Firm, P.C.

(57) ABSTRACT

A portable electronic device, a wearable device and methods for operating the same are provided. The portable electronic device includes a display, a communication interface that communicates with a wearable device using wireless short-range communication, and a processor that provides, via the display, a menu for controlling data of the wearable device, receives, via the communication interface, a security status from the wearable device, limits access to at least one item in the menu if the security status corresponds to a first security state, and allows access to the at least one item in the menu if the security status corresponds to a second security state.

11 Claims, 12 Drawing Sheets

(51) Int. Cl.
  *G06F 21/34*  (2013.01)
  *G06F 21/35*  (2013.01)
  *G06F 21/32*  (2013.01)
  *H04W 4/80*  (2018.01)
  *A61B 5/024*  (2006.01)
  *A61B 5/00*  (2006.01)
  *H04W 12/08*  (2009.01)
  *H04L 29/06*  (2006.01)

(52) U.S. Cl.
  CPC ............. *G06F 21/32* (2013.01); *G06F 21/34* (2013.01); *G06F 21/35* (2013.01); *G06F 21/6263* (2013.01); *H04L 63/0853* (2013.01); *H04W 4/80* (2018.02); *H04W 12/08* (2013.01); *H04L 63/0861* (2013.01)

(56) References Cited

U.S. PATENT DOCUMENTS

| | | | |
|---|---|---|---|
| 8,869,263 B2 | 10/2014 | Pasquero et al. | |
| 2004/0203414 A1 | 10/2004 | Satou et al. | |
| 2009/0249478 A1 | 10/2009 | Rosener et al. | |
| 2011/0214158 A1* | 9/2011 | Pasquero | G06F 21/35 726/2 |
| 2011/0296194 A1* | 12/2011 | Herkes | G06F 21/34 713/185 |
| 2013/0324045 A1* | 12/2013 | Shimohata | H04W 4/008 455/41.2 |
| 2016/0037346 A1* | 2/2016 | Boettcher | H04M 1/72519 455/411 |

FOREIGN PATENT DOCUMENTS

| | | |
|---|---|---|
| KR | 1020127023688 | 1/2013 |
| KR | 1020137002009 | 3/2013 |

* cited by examiner

METHOD FOR CONTROLLING SECURITY SYSTEM AND ELECTRONIC DEVICE THEREOF

PRIORITY

This application is a continuation application of U.S. patent application Ser. No. 14/528,744, filed with the U.S. Patent and Trademark Office on Oct. 30, 2014, claiming priority under 35 U.S.C. § 119(a) to Korean Patent Application Serial No. 10-2013-130471 filed in the Korean Intellectual Property Office on Oct. 30, 2013, the entire disclosure of each of which is incorporated herein by reference.

BACKGROUND

1. Field of the Invention

The present invention relates generally to a method for controlling a security system of an electronic device, and an electronic device thereof.

2. Description of the Related Art

As an electronic device, such as a smartphone, becomes more complicated and is used more frequently in daily life, the security of the electronic device becomes an issue. Hence, various security modes are implemented and a user frequently sets or releases a security level.

The security mode includes, for example, a screen lock function using a password or a pattern, a function for limiting corresponding application execution using the password or the pattern, a function for limiting access to a file such as document, MP3, or image file using the password or the pattern, a function for limiting access to an important setting item in an environment setting, and a function for limiting, during application installation, download of an application from a server other than a corresponding server.

According to the conventional art, the user manually sets and releases the security mode for the corresponding task if necessary. That is, the user sets a security type, password, or other method (e.g., the pattern) in advance and releases the security mode by inputting the preset password or pattern to use the electronic device. This frequently requires repeated operations, such that the user needs to repeatedly release the security mode even when the security mode is unnecessary.

SUMMARY

The present invention has been made to address at least the above-described problems and disadvantages, and to provide at least the advantages described below. Accordingly, an aspect of the present invention is to provide a method for applying status information of one or more secondary electronic devices for one system operation based on a security environment of a first electronic device, and the first and second electronic devices thereof.

In accordance with an aspect of the present invention, a portable electronic device is provided that includes a display, a communication interface configured to communicate with a wearable device using a wireless short-range communication, and a processor, which provides, via the display, a menu for controlling data of the wearable device. The processor receives, via the communication interface, a security status from the wearable device, limits access to at least one item in the menu if the security status corresponds to a first security state, and allows access to the at least one item in the menu if the security status corresponds to a second security state.

In accordance with another aspect of the present invention, a wearable device is provided that includes a sensor, a communication interface configured to communicate with a portable electronic device using wireless short-range communication, and a processor, which detects, via the sensor, a wearing status of the wearable device, determines a security status of the wearable device based on the wearing status, and transmits the security status to the portable electronic device.

In accordance with another aspect of the present invention, a method is provided for controlling a portable electronic device, with the method including displaying a menu for controlling data of a wearable device, receiving a security status from the wearable device, limiting access to at least one item of the menu if the security status is a first security state, and allowing access to the at least one item of the menu if the security status is a second security state.

BRIEF DESCRIPTION OF THE DRAWINGS

The above and other aspects, features, and advantages of certain embodiments of the present invention will be more apparent from the following description taken in conjunction with the accompanying drawings, in which.

Throughout the drawings, like reference numerals will be understood to refer to like parts, components and structures.

DETAILED DESCRIPTION OF EMBODIMENTS OF THE PRESENT INVENTION

Figure 1A:
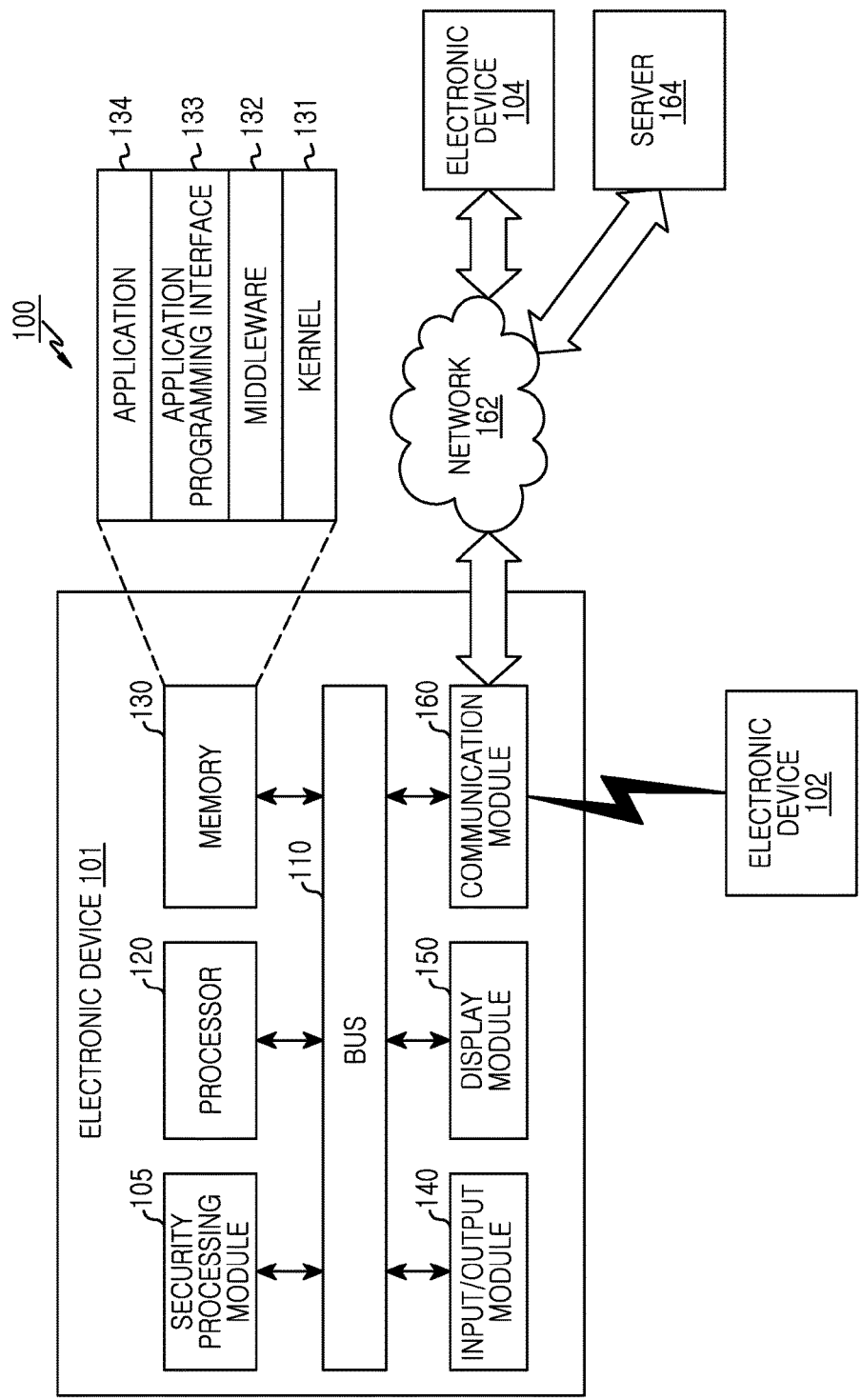
FIG. 1A is a block diagram of an electronic device, according to an embodiment of the present invention.

The following description with reference to the accompanying drawings is provided to assist in a comprehensive understanding of embodiments of the present invention as defined by the claims and their equivalents. It includes various specific details to assist in that understanding but these are to be regarded as merely illustrative. Accordingly, those of ordinary skill in the art will recognize that various changes and modifications of the embodiments described herein can be made without departing from the scope and spirit of the invention. In addition, descriptions of well-known functions and constructions may be omitted for clarity and conciseness.

The terms and words used in the following description and claims are not limited to their dictionary meanings, but are merely used to enable a clear and consistent understanding of the invention. Accordingly, it should be apparent to those skilled in the art that the following description of embodiments of the present invention is provided for illustrative purposes only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations, and other factors known to those of skill in the art, may occur in amounts that do not preclude the effect the characteristic was intended to provide.

An electronic device, according to the present invention can employ a device having a communication function. For example, the electronic device can include a smart phone, a tablet Personal Computer (PC), a mobile phone, a video phone, an Electronic-book reader (E-book reader), a desktop PC, a laptop PC, a netbook computer, a Personal Digital Assistant (PDA), a Portable Multimedia Player (PMP), an MP3 player, a mobile medical appliance, a camera, and a wearable device (e.g., at least one of a Head Mounted Display (HMD), such as electronic glasses, e-textile, an electronic bracelet, an electronic necklace, an electronic accessory, and a smart watch).

The electronic device can employ a smart home appliance having the communication function. The smart home appliance can include at least one of, for example, a television (TV), a Digital Versatile Disc (DVD) player, an audio system, a refrigerator, an air conditioner, a vacuum cleaner, an oven, a microwave oven, a washing machine, an air purifier, a set-top box, a TV box (e.g., Samsung HomeSync™, AppleTV™, or Google TV™), a game console, an electronic dictionary, a digital key, a camcorder, and a digital frame.

The electronic device can include at least one of medical appliances (e.g., Magnetic Resonance Angiography (MRA), Magnetic Resonance Imaging (MRI), Computed Tomography (CT), X-ray, ultrasonicator), a navigation device, a Global Positioning System (GPS) receiver, an Event Data Recorder (EDR), a Flight Data Recorder (FDR), an in-vehicle infotainment, marine electronic equipment (e.g., marine navigation device and gyro compass), avionics, and a security device.

The electronic device can include at least one of part of furniture or building/structure having the communication function, an electronic board, an electronic sign input device, a projector, and a gauge (e.g., water, electricity, gas, or radio signal).

The electronic device can include one or a combination of those various devices. Notably, one skilled in the art shall understand that the electronic device is not limited to those devices. Hereafter, the electronic device is explained by referring to the attached drawings. The term 'user' can indicate a person or a device (e.g., an artificial intelligence device) who or which uses the electronic device.

FIG. 1A is a block diagram of an electronic device, according to an embodiment of the present invention.

Referring to FIG. 1A, a first electronic device 101 is provided. The first electronic device 101 includes a security processing module 105, a bus 110, a processor 120, a memory 130, an input/output interface module 140, a display module 150, and a communication interface module 160.

The security processing module 105 controls to receive wearing status information obtained by a secondary electronic device 102. The security processing module 105 determines whether the wearing status information satisfies one or more preset conditions, and controls to determine a security level corresponding to the wearing status information, based on the preset condition satisfaction. The security processing module 105 determines a matching user profile among one or more user profiles recorded to the first electronic device 101, based on the wearing status information.

The security processing module 105 sets a user environment of the first electronic device 101, according to the determined security level or a security level of the user profile. The security processing module 105 is able to limit functions of the first electronic device 101 by considering the security level determined based on the wearing status information obtained by the secondary electronic device 102. The function limitation based on the security level can include a screen lock function using a password or a pattern, a function for limiting the corresponding application execution using the password or the pattern, a function for limiting file access to document, MP3, and image file using the password or the pattern, a function for limiting accessibility of important setting items in the environment setting, and a function for limiting, during application installation, application downloads from a server other than a corresponding server.

The security processing module 105 detects wearing status change of the secondary electronic device 102 during the operation of the first electronic device 101, and changes the security environment (or the security level) of the first electronic device 101, according to the wearing status change.

The bus 110 is a circuit for interlinking the above-stated components and transferring communication (e.g., control messages) between the components.

The processor 120 receives an instruction from the other components (e.g., the memory 130, the input/output interface module 140, the display module 150, and the communication interface module 160) of the first electronic device 101 via the bus 110, interprets the received instruction, and performs an operation or a data processing according to the interpreted instruction.

The memory 130 stores the instruction or the data received from or generated by the processor 120 or the other components (e.g., the input/output interface module 140, the display module 150, and the communication interface module 160). For example, the memory 130 can include programming modules including a kernel 131, middleware 132, an Application Programming Interface (API) 133, and an application 134. The programming modules can be implemented using software, firmware, and hardware, or a combination of at least two of them.

The kernel 131 controls or manages system resources (e.g., the bus 110, the processor 120, or the memory 130) used to execute the operation or the function of the other programming modules, for example, the middleware 132, the API 133, and the application 134. The kernel 131 can provide an interface allowing the middleware 132, the API 133, or the application 134 to access and control or manage the individual component of the first electronic device 101.

The middleware 132 relays data between the API 133 or the application 134 and the kernel 131. The middleware 132 can perform load balancing of work requests received from the applications 134 by giving priority of the system resource (e.g., the bus 110, the processor 120, or the memory 130) of the first electronic device 101 to at least one of the applications 134.

The API 133, which is an interface for the application 134 to control the kernel 131 or the middleware 132, can include at least one interface or function for file control, window control, image processing, or text control.

The input/output interface module 140 receives and forwards the instruction or the data from the user to the processor 120 or the memory 130 via the bus 110. The display module 150 displays an image, a video, or data to the user. When the display module 150 is a touch screen panel, the instruction can be input using a gesture which touches or hovers over (e.g., indirectly touches) the display module 150.

The communication interface module 160 connects the communication between the first electronic device 101 and the secondary electronic devices 102 or between an electronic device 104 and a server 164. The communication interface module 160 can support short-range communication protocol (e.g., Wi-Fi, Bluetooth (BT), Near Field Communication (NFC)), or a communication network 162 (e.g., Internet, Local Area Network (LAN), Wide Area Network (WAN), telecommunication network, cellular network, satellite network, or Plain Old Telephone Service (POTS)). The electronic devices 102 and 104 can be the same as or different from the first electronic device 101.

Figure 1B:
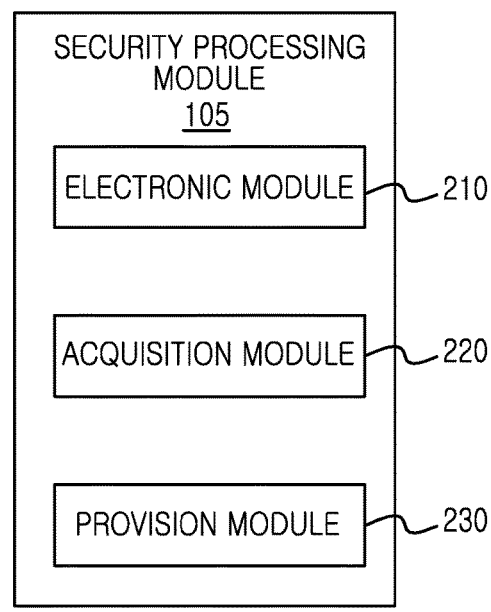
FIG. 1B is a block diagram of a security processing module of an electronic device, according to an embodiment of the present invention.

FIG. 1B is a block diagram of a security processing module of a first electronic device 101, according to an embodiment of the present invention.

Referring to FIG. 1B, the security processing module 105 includes one or more of a detection module 210, an acquisition module 220, and a provision module 230.

The detection module 210 detects the wearing status change of the secondary electronic device 102 based on the wearing status information received from the secondary electronic device 102. The secondary electronic device 102 periodically sends its wearing status information to the first electronic device 101, and the first electronic device 101 detects the wearing status change of the secondary electronic device 102 based on one or more wearing status information received.

The acquisition module 220 receives the wearing status information acquired by the secondary electronic device 102 or the security level and user profile determined based on the wearing status information. The acquisition module 220 receives the wearing status information of the secondary electronic device 102 or the security level and user profile determined, based on the wearing status information, from the connected secondary electronic device 102 through a communication module for one or more network communications of the first electronic device 101.

The provision module 230 provides the first electronic device 101 with the user environment corresponding to the security level of the information acquired by the secondary electronic device 102. The provision module 230 provides a menu for inputting an identification code, such as password or pattern, required to operate the first electronic device 101 according to the determined user environment. During operation of the first electronic device 101, the provision module 230 periodically refers to the wearing status information or the network communication environment of the secondary electronic device 102. When detecting abnormality of the wearing status of the electronic device 102 or the data transmission/reception of the network communication, the provision module 230 controls the security level of the first electronic device 101 in a predetermined manner.

Figure 2:
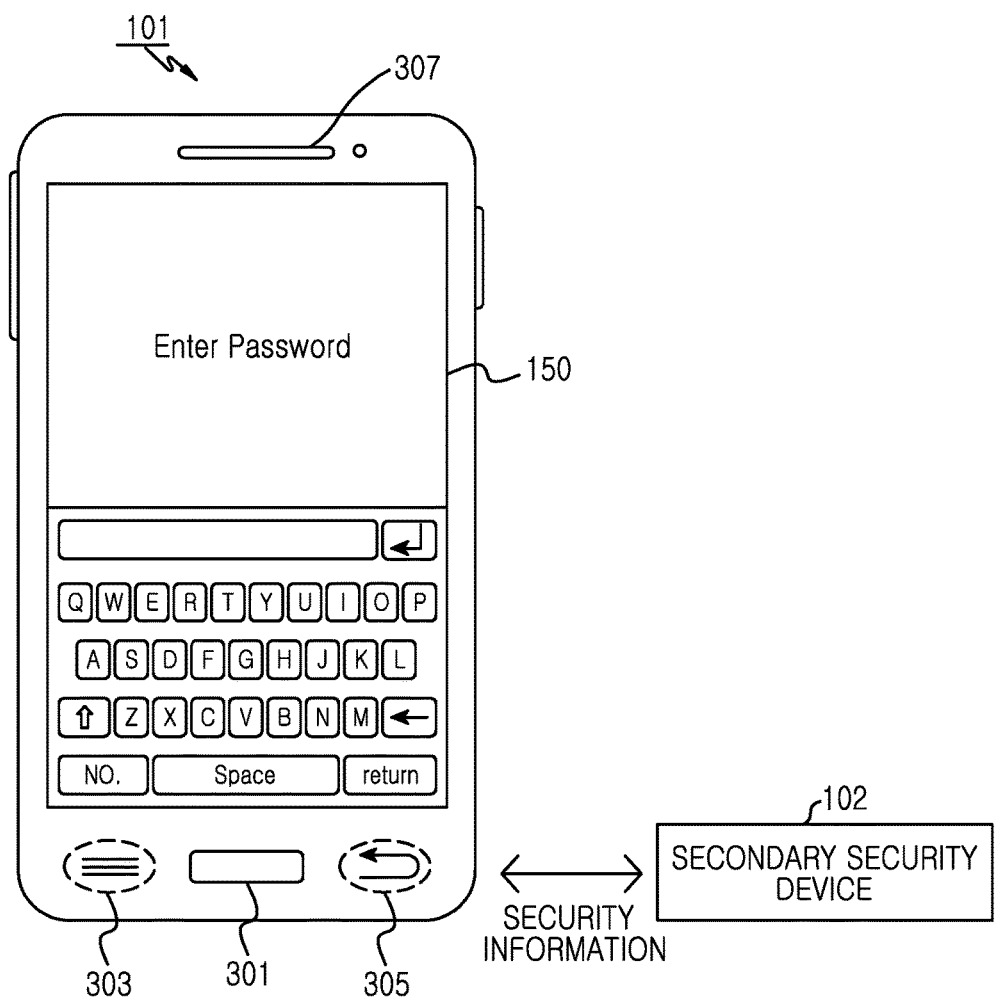
FIG. 2 illustrates a first electronic device and a secondary electronic device, according to an embodiment of the present invention.

FIG. 2 illustrates a first electronic device and a secondary electronic device, according to an embodiment of the present invention.

Referring to FIG. 2, the first electronic device 101 includes a speaker 307 for outputting sound, a button 301 on an upper side, a lower side, a front side, or a back side, as one of input devices for inputting an instruction by clicking the button 301, and a touch button 303 or 305 at a fixed location for inputting an instruction through the touch. The first electronic device 101 can include at least one microphone (not shown) for inputting an external sound of the first electronic device 101 at a location exposed outside the first electronic device 101 for the sound input. The first electronic device 101 can include the display module 150 on its front side, and display its User Interface (UI) operation through the display module 150.

While the speaker 307, the button 301, or the touch button 303 or 305 are not depicted, the secondary electronic device 102 can include speaker 307, the button 301, or the touch button 303 or 305 at the same locations or at different locations.

Referring to FIG. 2, the first electronic device 101 can change its security level based on a preset input. When the display module 150 is turned on, the first electronic device 101 provides a menu for changing the highest security level. The first electronic device 101 provides a region for inputting the password on the display module 150 being turned on. The password can be input to the first electronic device 101 in various manners using, for example, a region for inputting characters, symbols, numbers, or a character string combining one or more of them, a region for inputting the pattern, or sound input.

To change the security level, the first electronic device 101 can also apply the security function of one or more secondary electronic devices 102 connected through the network communication. When changing the security level at the point of an active mode (e.g., the turn-on of the display module 150), the first electronic device 101 receives security level from the one or more connected secondary electronic devices 102. The secondary electronic device 102 can be a wearable electronic device. When the secondary electronic device 102 is worn, the first electronic device 101 checks the wearing status and determines whether the wearing status information satisfies the condition which defines the security level. The first electronic device 101 obtains the wearing status information of the secondary electronic device 102 through one or more sensors attached. The first electronic device 101 receives the wearing status information from the secondary electronic device 102, and determine whether the use of the first electronic device 101 is authorized based on the wearing status information. When the display module 150 is turned on and the wearing status information received from the secondary electronic device 102 is the status information approving the use of the first electronic device 101, the first electronic device 101 provides the menu for changing its security level, such as password input region. When a correct password is input, the first electronic device 101 may lower its security level or switch to the security level not limiting its use. While the secondary electronic device 102 is worn, the changed security level of the first electronic device 101 is maintained.

Alternatively, the first electronic device 101 determines the user of the secondary electronic device 102 based on the wearing status information received from the secondary electronic device 102, and provides the user profile corresponding to the user. The first electronic device 101 can set profiles of one or more users (e.g., a first user and a second user). When the wearing status information from the secondary electronic device 102 relates to the first user, the first electronic device 101 applies the user profile to the first user. When the display module 150 is turned on, the first electronic device 101 provides the password input region applied to the first user. When the password corresponding to the first user is input correctly, the first electronic device 101 may change the first user profile security level.

When the password of the second user or an incorrect password is input to the password input region while the secondary electronic device 102 is worn by the first user, the first electronic device 101 does not allow a change of the security level by the user and changes the security level to the highest level for limiting the first electronic device 101. When the wearing status information received from the secondary electronic device 102 indicates that the secondary electronic device 102 is not being worn or the user profile is not designated (e.g., incorrect wearing), the first electronic device 101 does not provide a password input region for changing the security level and changes the security level to the highest level, which may be done automatically.

While the first electronic device 101 can determine the user profile based on the wearing status information received from the secondary electronic device 102, the first electronic device 101 may receive the user profile determined based on the wearing status information from the secondary electronic device 102 and set the user environment based on the user profile. When the secondary electronic device 102 sends the user profile to the first electronic device 101 and shares the same user information with the first electronic device 101, the secondary electronic device 102 may send an identification code indicative of the user profile as the user profile. When the secondary electronic device 102 sends the user profile including additional information which is not included in the first electronic device 101, the user profile can include a preset protocol data for the first electronic device 101, and the first electronic device 101 applies the received information.

Figure 3A:
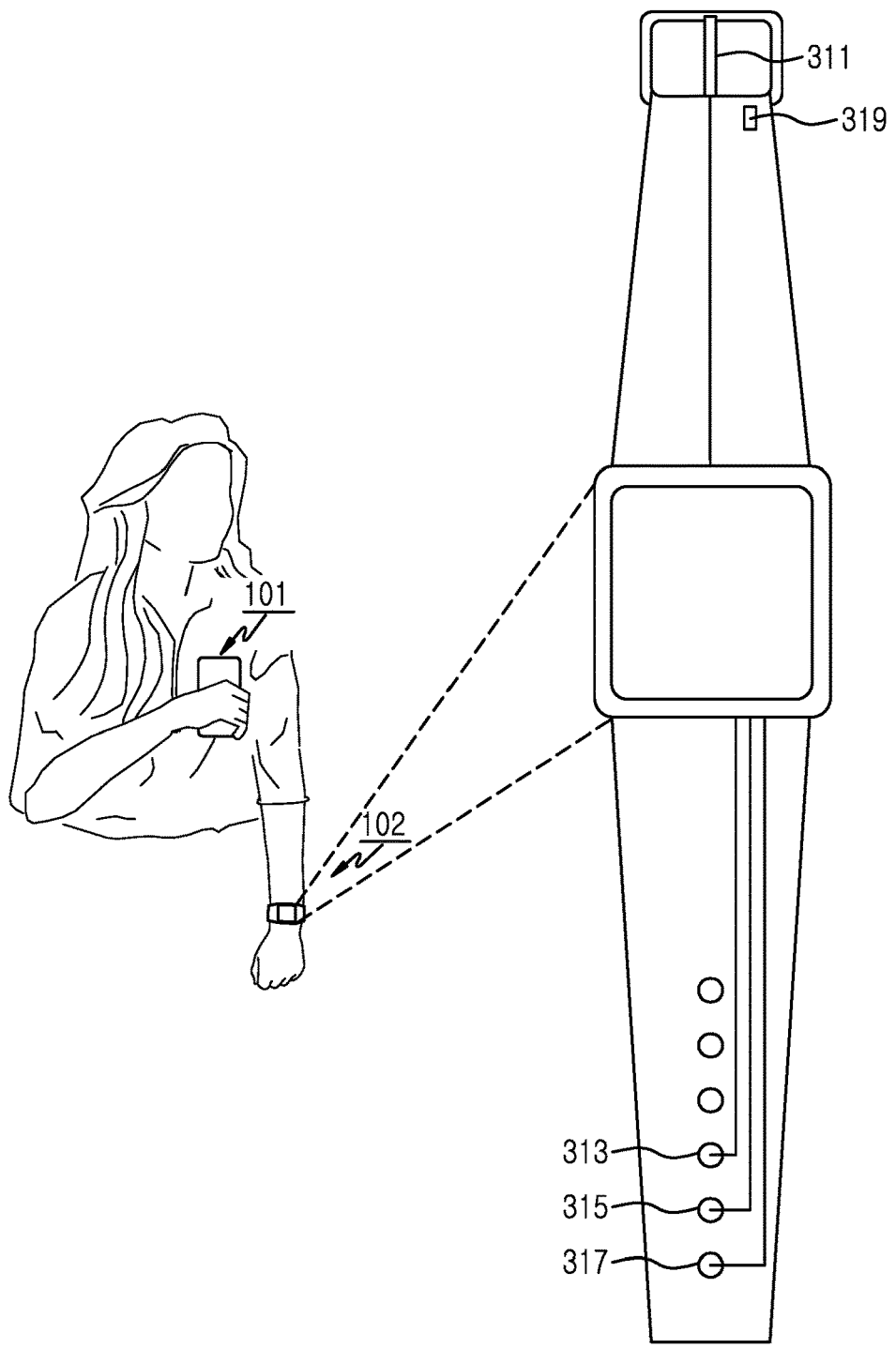
FIGS. 3A, 3B and 3C illustrate the security processing by a first electronic device connected with a secondary electronic device attached to a wrist strap, according to an embodiment of the present invention.
Figure 3B:
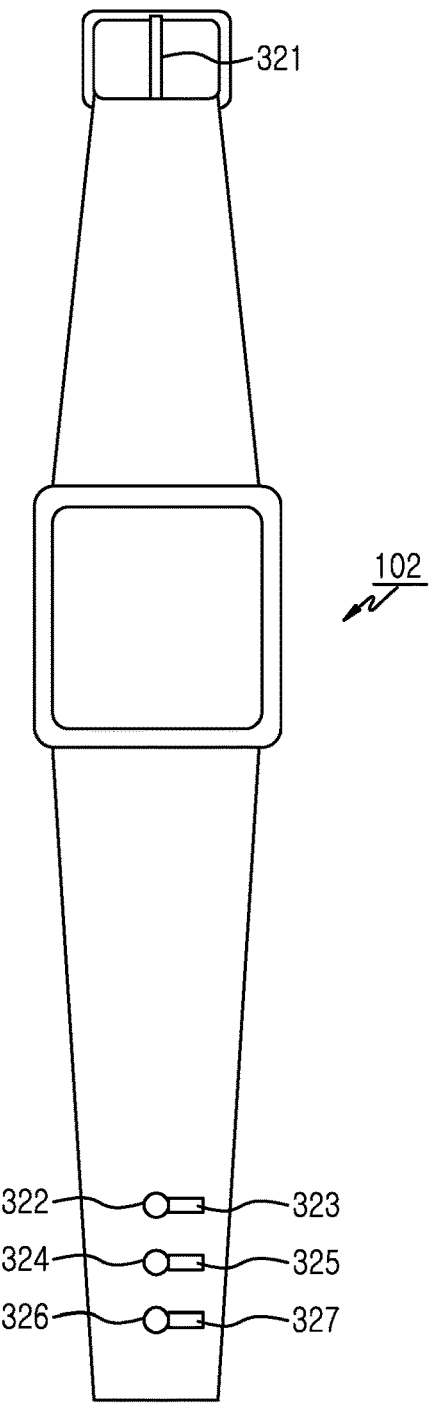
Figure 3C:
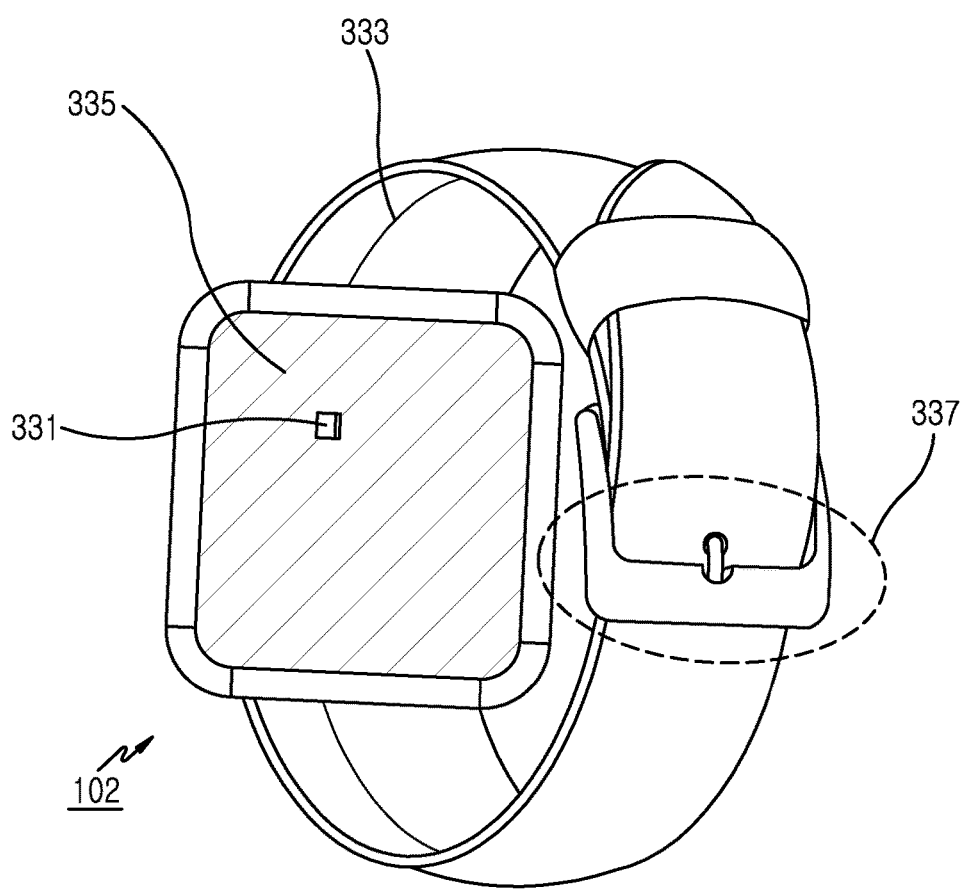

FIGS. 3A, 3B and 3C illustrate the security processing by a first electronic device connected with a secondary electronic device attached to a wrist strap, according to an embodiment of the present invention.

Referring to FIGS. 3A, 3B and 3C, the secondary electronic device 102 can be a device attached to a strap, such as wrist watch.

Referring to FIG. 3A, the strap of the secondary electronic device 102 is fastened by fitting a tongue 311 of a buckle into a hole 313, 315, or 317. To determine the wearing status of the secondary electronic device 102, when the secondary electronic device 102 is the wrist watch, the buckle tongue and the holes can be connected to a main body of the secondary electronic device 102 using a conducting wire mounted at a preset location of the strap. When the hole 313, 315, or 317 of the strap of the secondary electronic device 102 is fastened to the tongue 311, it can be designed to flow a preset current quantity (a preset resistance of the hole) through the hole or to generate a preset connection signal (e.g., an electromagnetic signal), and detect the fastened buckle through a module (e.g., a module for detecting the connection through resistance or a ground (GND) component) for detecting whether the buckle is correctly fastened. After determining the connection through the module, a dual structure may determine the connection status of the tongue and the hole. When the tongue is fastened to one hole, the secondary electronic device 102 obtains the wearing status information from the current quantity or the connection signal of the hole. The secondary electronic device 102 sends the wearing status information to the first electronic device 101, and the first electronic device 101 determines the user of the secondary electronic device 102 based on the obtained wearing status information. The secondary electronic device 102 determines the user profile based on the obtained wearing status information. For example, when the tongue 311 is fastened to the hole 313 of the strap, the secondary electronic device 102 retrieves the preset user information from its database based on the acquired current quantity or connection signal. When the obtained current quantity or connection signal satisfies first user information, the secondary electronic device 102 sends the first user profile to the first electronic device 101. Further, the secondary electronic device 102 may retrieve the preset user information with the obtained current quantity or connection signal or sensor information obtained by one or more sensors. Even when the tongue and the hole of the strap are fastened, the secondary electronic device 102 can obtain its temperature or an object temperature through a temperature sensor. When the obtained temperature corresponds to a preset temperature range of an external electronic device, the secondary electronic device 102 determines the user information corresponding to the obtained current quantity or connection signal.

The first electronic device 101 receives the wearing status information or the user profile determined based on the wearing status information from the secondary electronic device 102. Upon receiving the wearing status information, the first electronic device 101 determines the user profile including the wearing status information in its database based on the wearing status information. The first electronic device 101 determines its security level according to the user profile and provides a function according to the security level. For example, for the first user profile, the first electronic device 101 provides a menu for inputting a password when the display module 150 is turned on, and may lower the security level when the correct password is input. When the preset user information is not input, the first electronic device 101 detects the input for turning on the display module 150 at the security level which locks the first electronic device 101, and receives the first user profile from the connected secondary electronic device 102 when the display module 150 is turned on. The first electronic device 101 provides a menu for inputting the password according to the first user profile received. When the correct password is input, the first electronic device 101 releases the lock function and provides the security level function (e.g., change the security level) corresponding to the first user profile. When an incorrect password is input, the first electronic device 101 stays in the lock mode and prevents access by the first user.

When the correct password is input and the wearing status of the secondary electronic device 102 is changed or the network communication remains connected to the first electronic device 101 at the security level corresponding to the user information, the first electronic device 101 maintain the current security level though the display module 150 is turned off.

When the network communication is disconnected from the secondary electronic device 102, the data transmission falls below a preset level, or the correct buckle connection is not detected due to the damaged strap of the secondary electronic device 102 or the damaged secondary electronic device 102, the first electronic device 101 changes its security level to the original security level or a higher security level through the password input.

Referring to FIG. 3B, the secondary electronic device 102 can include a module 323, 325, or 327 for detecting a tongue 321 of the buckle fitting into a hole 322, 324, or 326 of the strap, at a preset location based on the hole. For example, when the buckle tongue 321 is fastened to one (e.g., the hole 322 connected to the module 323) of the one or more holes of the strap, the module 323 sends a preset signal of the hole 322 to the main body of the secondary electronic device 102 through a preset conducting wire of the strap. The secondary electronic device 102 determines the security level corresponding to the preset signal obtained by the module 323, and sends the security level to the first electronic device 101 connected via the network communication. The first electronic device 101 controls its content security level based on the obtained security level.

Referring to FIG. 3C, besides the information obtained from the connection of the buckle tongue and the hole, the secondary electronic device 102 can obtain its wearing status information through one or more sensors connected. The secondary electronic device 102 can include one or more of a proximity sensor, a touch sensor, a grip sensor, a wave (pulse or pulse wave) sensor, a temperature sensor, a fingerprint sensor, and a tension sensor, and obtain its status information (e.g., wearing status information) from the attached sensor. The secondary electronic device 102 can include a proximity sensor 331 at a preset location (e.g., on the back side of the main body of the secondary electronic device 102) of the main body or the strap. When the secondary electronic device 102 is worn, the proximity sensor 331 can obtain a signal corresponding to the wearing status of the secondary electronic device 102. Alternatively, the secondary electronic device 102 can include a temperature sensor 333 at a preset location (e.g., in a region contacting the object when the strap of the secondary electronic device 102 is fastened) of the main body or the strap. When the secondary electronic device 102 is worn, the temperature sensor 333 can obtain temperature information of the object wearing the secondary electronic device 102. Alternatively, the secondary electronic device 102 can include a grip sensor 335 at a preset location (e.g., in a region contacting the object when the strap of the secondary electronic device 102 is fastened) of the main body or the strap. When the secondary electronic device 102 is worn, the grip sensor 335 obtains contact information of the object wearing the secondary electronic device 102. The grip sensor 335 may obtain an electromagnetic signal pattern of the contacted object.

The secondary electronic device 102 or the first electronic device 101 can determine the preset user information (e.g., the user profile) using one or more sensor information obtained by the secondary electronic device 102, and can also determine the security level corresponding to the obtained sensor information. The first electronic device 101 can provide a security service by additionally applying content provision based on the determined user information or security level.

Figure 4:
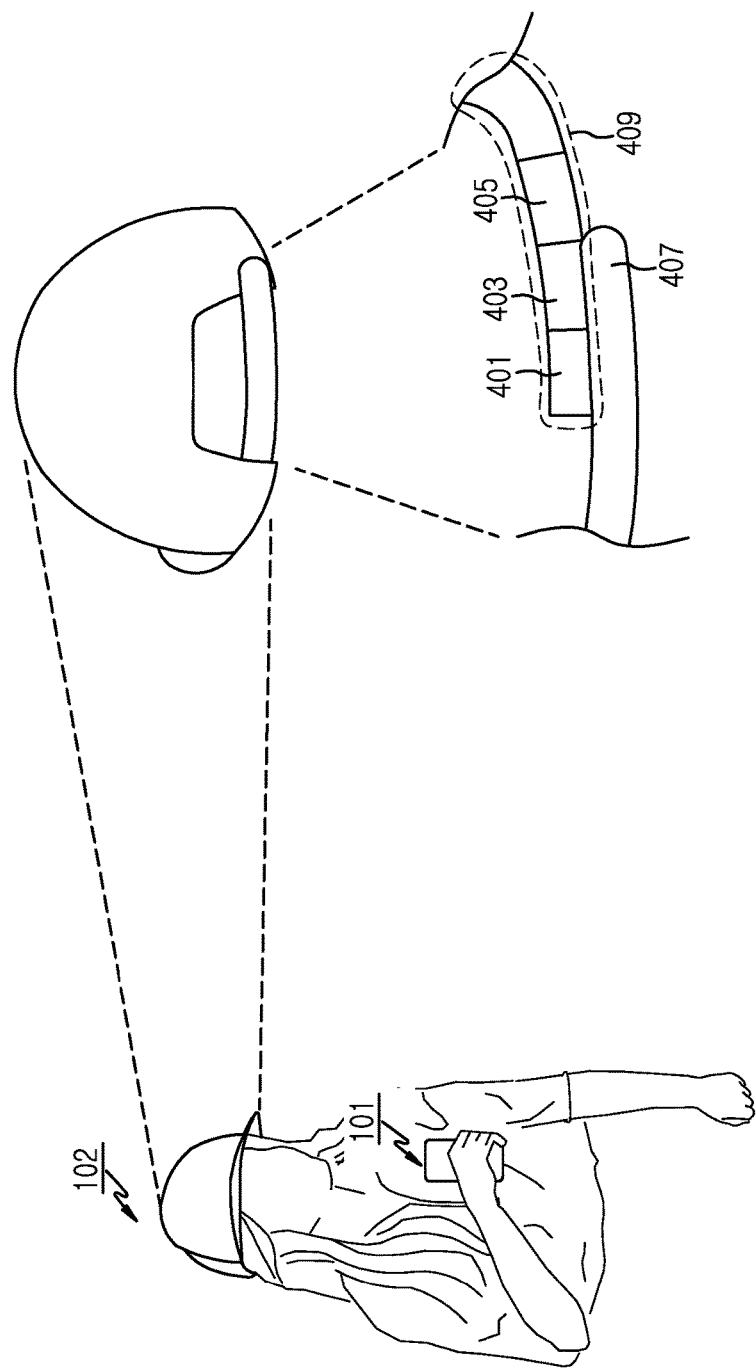
FIG. 4 illustrates the security processing by a first electronic device connected with a secondary electronic device attached to a hat, according to an embodiment of the present invention.

FIG. 4 illustrates the security processing of an electronic device connected with a secondary electronic device attached to a hat, according to an embodiment of the present invention.

Referring to FIG. 4, the secondary electronic device 102 can be a wearable device including a band for adjusting the size or a device attached to wearable clothes, shoes, hats, gloves, or accessories. When the secondary electronic device 102 is attached to a hat, the bands of the hat can be secured by attaching or fastening two or more bands, such as Velcro to one or more regions of the band. For example, a first band 407 contains preset regions, rather than a fixed location, for attaching a second band. The second band 409 contains specified regions, such as a first region 401, a second region 403, and a third region 405. In the secondary electronic device 102 attached to the hat for adjusting the size using two bands, when part of preset regions of a first band 407 and one of the regions (e.g., the first region 401, the second region 403, or the third region 405) of the second band 409 are coupled, the secondary electronic device 102 can be designed to flow the current or to issue the connection signal corresponding to the first region 401, the second region 403, or the third region 405 of the second band 409. When the first band 407 and the second band 409 are fastened, the secondary electronic device 102 obtains the corresponding current or connection signal and the wearing status information through its one or more sensors attached to the hat. The secondary electronic device 102 obtains the wearing status information through one or more sensors for checking the wearing status of the hat, such as proximity sensor, touch sensor, and temperature sensor. The secondary electronic device 102 sends, to the first electronic device 101, the sensor information, obtained from the connected one or more sensors of the secondary electronic device 102 attached to the hat, and the wearing status information. The first electronic device 101 determines the user profile based on the received wearing status information. The first electronic device 101 determines whether the hat, including the secondary electronic device 102, is worn, based on the received wearing status information obtained from the sensor information measured by the one or more sensors connected to the secondary electronic device 102. When the hat including the secondary electronic device 102 is worn, the first electronic device 101 determines the user profile based on the current quantity or connection signal information obtained from the connection of the first band 407 and the second band 409. To determine the user profile, the first electronic device 101 or the secondary electronic device 102 includes the user profile corresponding to the current quantity or the connection signal information when the preset region of the first band 407 and the first region 401 of the second band 409 are fastened, the current flow or the connection signal information when the preset region of the first band 407 and the second region 403 of the second band 409 are fastened, and the current flow or the connection signal information when the preset region of the first band 407 and the third region 405 of the second band 409 are fastened. That is, when the hat including the secondary electronic device 102 is worn, the first electronic device 101 determines the user profile corresponding to the connection of the preset region of the first band 407 and the first region 401, the second region 403, or the third region 405 of the second band 409 and based on the wearing status information. Alternatively, when the hat is worn, the secondary electronic device 102 sends to the first electronic device 101 the determined user profile corresponding to the connection of the preset region of the first band 407 and the first region 401, the second region 403, or the third region 405 of the second band 409 and based on the wearing status information.

Based on the wearing status information of the secondary electronic device 102 connected via the network communication, the first electronic device 101 is able to control its security level change. When the wearing status information of the secondary electronic device 102 corresponds to the user authorized to control the security level of the first electronic device 101, the first electronic device 101 is able to change its security level according to a security level change command input. When changing the security level according to the input command, the first electronic device 101 is able to limit the change of the security level based on the security level corresponding to the user profile determined by the wearing status information of the secondary electronic device 102.

Figure 5:
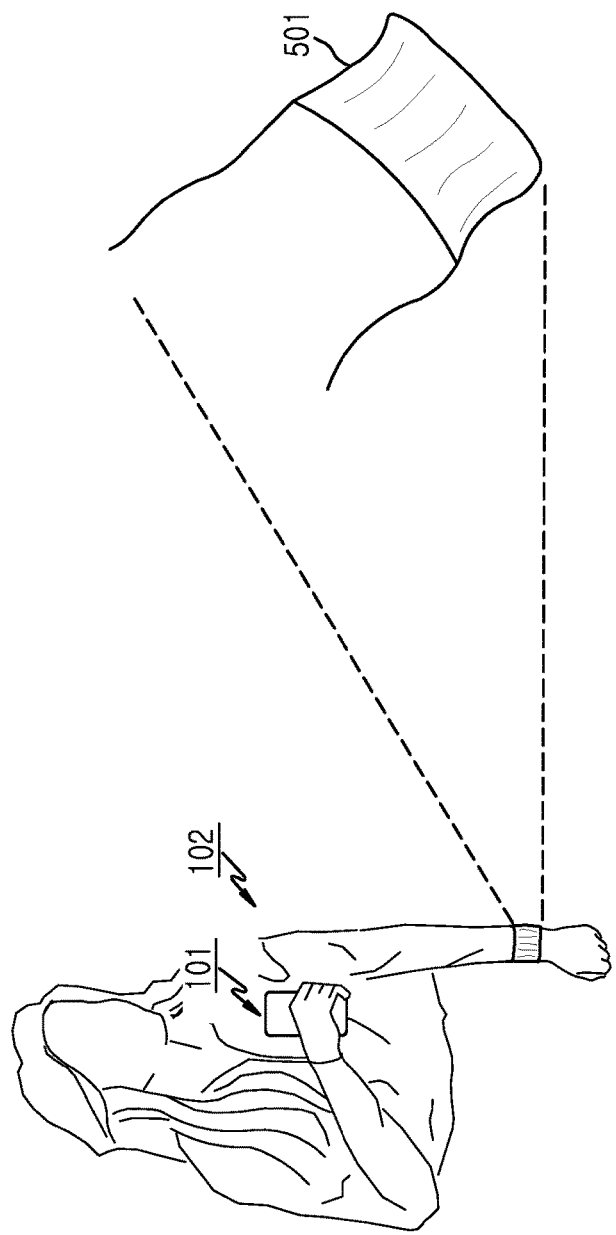
FIG. 5 illustrates the security processing by a first electronic device connected with a secondary electronic device attached to a wristband of clothing, according to an embodiment of the present invention.

FIG. 5 illustrates the security processing by an electronic device connected with a secondary electronic device attached to a wristband of clothing, according to an embodiment of the present invention.

Referring to FIG. 5, the secondary electronic device 102 can be a wearable device including a band for adjusting the size according to the tension, or a device attached to wearable clothes, shoes, hats, gloves, or accessories. When the secondary electronic device 102 is attached to clothes, a wristband 501 of the clothes can adjust its size using the tension from the part of the body passing through the wristband 501. In the secondary electronic device 102 attached to the clothes including the wristband 501 size-adjusted by the tension, the secondary electronic device 102 can be designed to flow the current or to issue the connection signal so as to measure a value corresponding to the preset tension of the wristband 501. The secondary electronic device 102 obtains the wearing status information from the current quantity or the connection signal corresponding to the tension of the wristband 501 and one or more sensors attached to the clothes. The secondary electronic device 102 obtains the wearing status information from one or more sensors for checking the wearing status of the clothes, such as a proximity sensor, a touch sensor, and a temperature sensor. The secondary electronic device 102 sends to the first electronic device 101 the sensor information obtained from its connected one or more sensors attached to the clothes, the value corresponding to the tension applied to a tension sensor of the wristband 501, and the wearing status information such as current quantity or connection signal. The first electronic device 101 determines the user profile based on the received wearing status information.

The first electronic device 101 can determine whether the clothes, including the secondary electronic device 102 is worn, based on received wearing status information obtained from the sensor information measured by the one or more sensors connected to the secondary electronic device 102. When the clothes, including the secondary electronic device 102 are worn, the first electronic device 101 determines the user profile based on the tension information applied to the tension sensor of the secondary electronic device 102.

Figure 6:
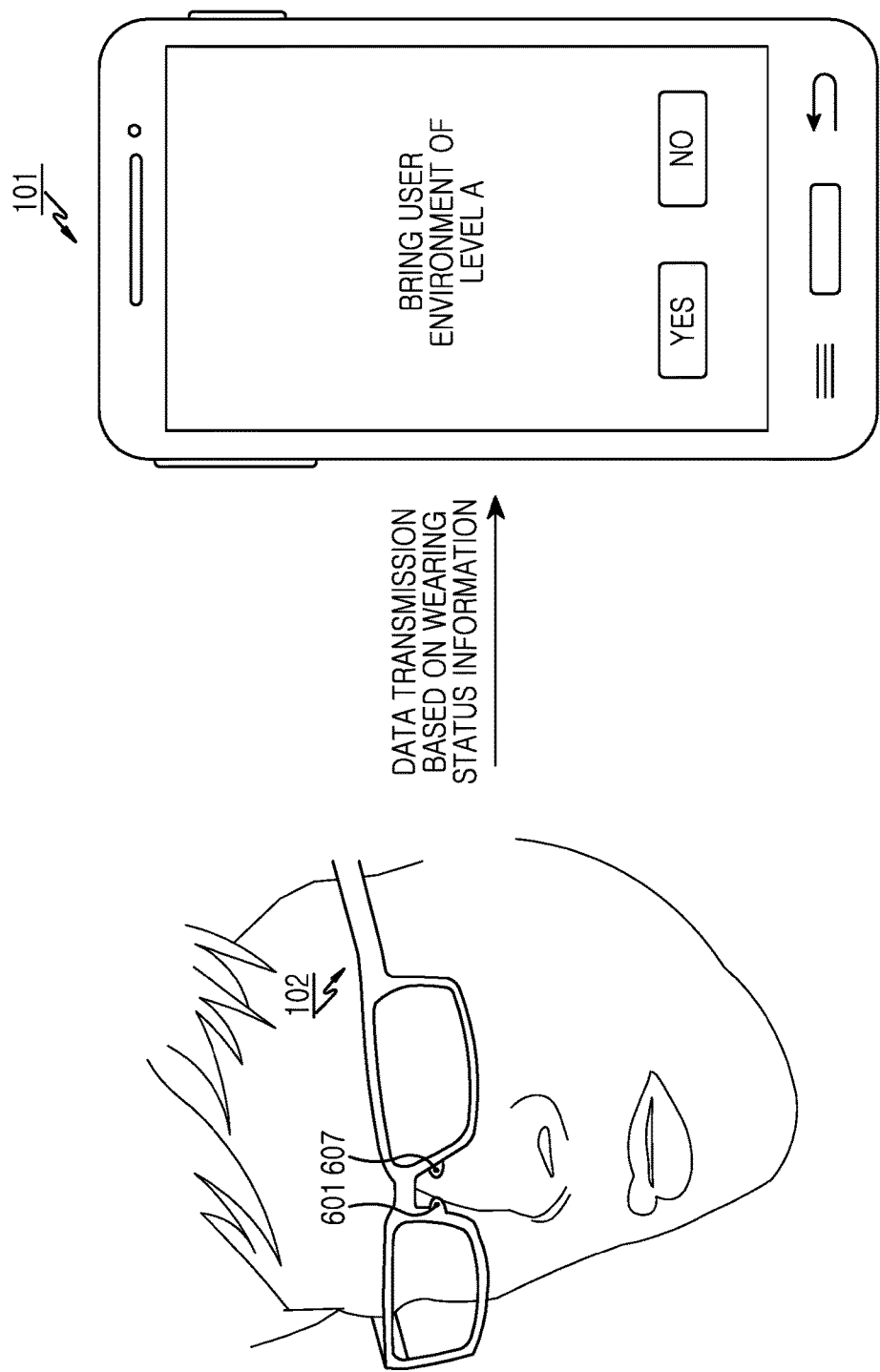
FIG. 6 illustrates the security processing by a first electronic device connected with a secondary electronic device attached to eyeglasses, according to an embodiment of the present invention.

FIG. 6 illustrates the security processing by an electronic device connected with a secondary electronic device 102 attached to eyeglasses, according to an embodiment of the present invention.

Referring to FIG. 6, the secondary electronic device 102 can be a device attached to wearable clothes, shoes, hats, gloves, or accessories. For example, the secondary electronic device 102 can be eyeglasses or a device attached to a preset location of the eyeglasses together with one or more sensors. When the secondary electronic device 102 is attached to the eyeglasses, the secondary electronic device 102 obtains the wearing status information of the eyeglasses from a tension sensor for measuring the tension applied to a frame of the eyeglasses being worn, and a temperature sensor attached to a preset location (e.g., at the temples or a bridge 601 or 607) of the eyeglass frame.

The first electronic device 101 or the secondary electronic device 102 determines the user profile based on the obtained wearing status information. For example, the first electronic device 101 determines the user profile satisfying the tension value obtained by the tension sensor and the temperature measured by the temperature sensor, by referring to the wearing status information of the secondary electronic device 102. For example, the secondary electronic device 102 provides the determined user profile to the first electronic device 101 and reinforces the security of the first electronic device 101.

The first electronic device 101 provides a security environment corresponding to the determined user profile. The first electronic device 101 can display a service based on the security level corresponding to the user profile determined based on the wearing status information when the display module 150 is turned on. For example, the first electronic device 101 can display a lock screen of the determined security level on the display module 150, and release the lock screen according to a user's input. The first electronic device 101 is able to change the security level by releasing the lock screen. When the wearing status information of the secondary electronic device 102 stays below a preset value or an error range, the security level of the first electronic device 101 is maintained. For example, the first electronic device 101 provides a menu for inputting a password or a pattern to change the security level on the screen when the display module 150 is turned on, and changes the security environment at the preset security level by receiving an input of the correct password or pattern. When the display module 150 of the first electronic device 101 is turned off, the first electronic device 101 returns to the original security level prior to input of the password or pattern. In this case, at the security level of the user profile determined based on the wearing status information of the connected secondary electronic device 102, the first electronic device 101 changes its security level according to the authority based on the wearing status information of the secondary electronic device 102. When the wearing status of the secondary electronic device 102 does not change and the display module 150 of the first electronic device 101 is turned off, the first electronic device 101 maintains the lock release (e.g., the changed security level) without changing the security level according to the setting.

At the security level of the user profile determined based on the wearing status information of the secondary electronic device 102 connected, when the wearing status information of the secondary electronic device 102 is switched to the wear release or the wearing status of the secondary electronic device 102 is changed, for example, when the first electronic device 101 and the secondary electronic device 102 are disconnected (e.g., the disconnection of the network communication), the security level of the first electronic device 101 can be changed to the security level before the lock release or to the preset security level (e.g., the highest security level).

Alternatively, the first electronic device 101 can notify a user of the wearing status information of the secondary electronic device 102 by displaying the wearing status change information of the secondary electronic device 102 through the display module 150, outputting the sound indicative of the wearing status change through a speaker, or vibrating in a preset pattern.

Figure 7:
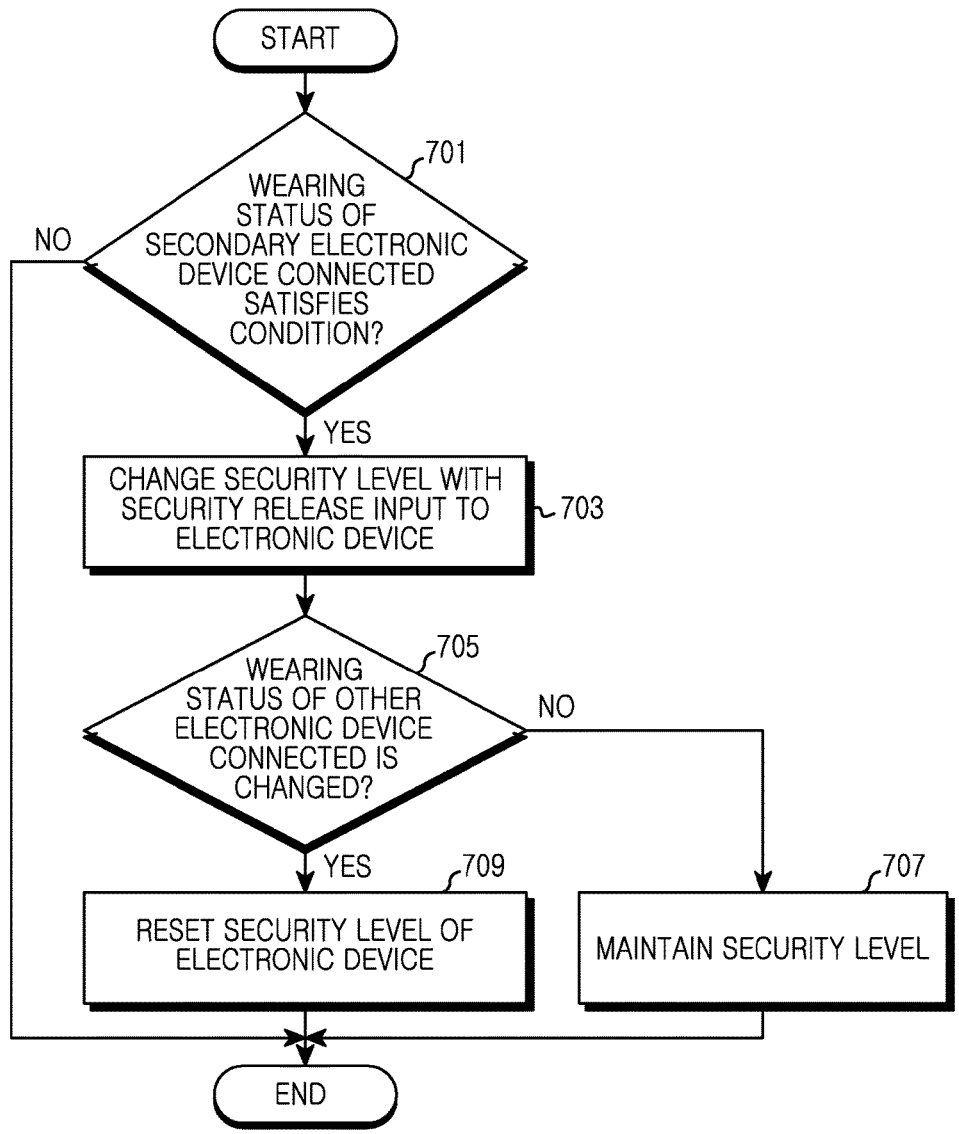
FIG. 7 is a flowchart of a security processing method of an electronic device, according to an embodiment of the present invention.

FIG. 7 is a flowchart of a security processing method of an electronic device, according to an embodiment of the present invention.

The first electronic device 101 is able to control its security level based on the wearing status information or the user profile received from the secondary electronic device 102.

In step 701, the first electronic device 101 determines whether the wearing status information obtained by the wearable secondary electronic device 102 connected via the network communication satisfies a preset condition. For example, the secondary electronic device 102 obtains the wearing status information through one or more sensors. The first electronic device 101 or the secondary electronic device 102 determines whether the obtained wearing status information satisfies one or more preset conditions for controlling the security level in the security environment of the first electronic device 101. If the obtained wearing status information satisfies one or more preset conditions for controlling the security level, then the electronic device proceeds to step 703. If one or more preset conditions for controlling the security level is not satisfied, then the process ends.

In step 703, the first electronic device 101 determines the security level according to the condition satisfied by the wearing status information of the secondary electronic device 102. The first electronic device 101 determines whether the wearing status information of the secondary electronic device 102 satisfies one or more security levels of the first electronic device 101, and provides the user environment at the determined security level.

The first electronic device 101 checks the authority for providing the user environment at the security level determined by the secondary electronic device 102. For example, the first electronic device 101 receives an identification code, such as a password or pattern, for accessing the user environment at the security level. When the input identification code is correct, the first electronic device 101 provides the authorized user environment at the security level.

In step 705, the first electronic device 101 or the secondary electronic device 102 determines whether the wearing status of the secondary electronic device 102 is changed during the operation of the first electronic device 101 according to the authorized security level. For example, when the preset condition is or is not satisfied at the preset location such as buckle (pin or hole) or tension sensor, the secondary electronic device 102 sends, to the first electronic device 101, the changed wearing status information or the security level determined based on the wearing status information. Alternatively, the first electronic device 101 detects an error (e.g., disconnection) of the data transmission/reception of the network communication with the secondary electronic device 102 during its operation according to the granted authority of the determined security level.

When detecting a change of the wearing status information or the network communication of the secondary electronic device 102, the first electronic device 101 proceeds to step 709. Otherwise, the first electronic device 101 proceeds to step 707.

In step 707, when the wearing status of the secondary electronic device 102 does not change, the first electronic device 101 maintains the current security level and security environment during the operation at the determined security level. For example, when the display module 150 is turned off, the first electronic device 101 maintains the security release according to the setting which controls to change the security level of the security release (the security status of the first electronic device 101 with the granted authority) to the security level of the lock, without locking the security level.

In step 709, the first electronic device 101 resets the security level. When detecting the changed wearing status of the secondary electronic device 102 at the current security level (e.g., the security level of the first electronic device 101 with the authority authorized according to the identification code), the first electronic device 101 changes its security level. For example, when the secondary electronic device 102 is taken off while at a low security level according to the identification code, the first electronic device 101 changes the security level to the highest security level. When changing the security level to the highest security level, the first electronic device 101 may output information indicating that the secondary electronic device 102 has been taken off.

After step 707 or 709, the process of FIG. 7 ends.

Figure 8:
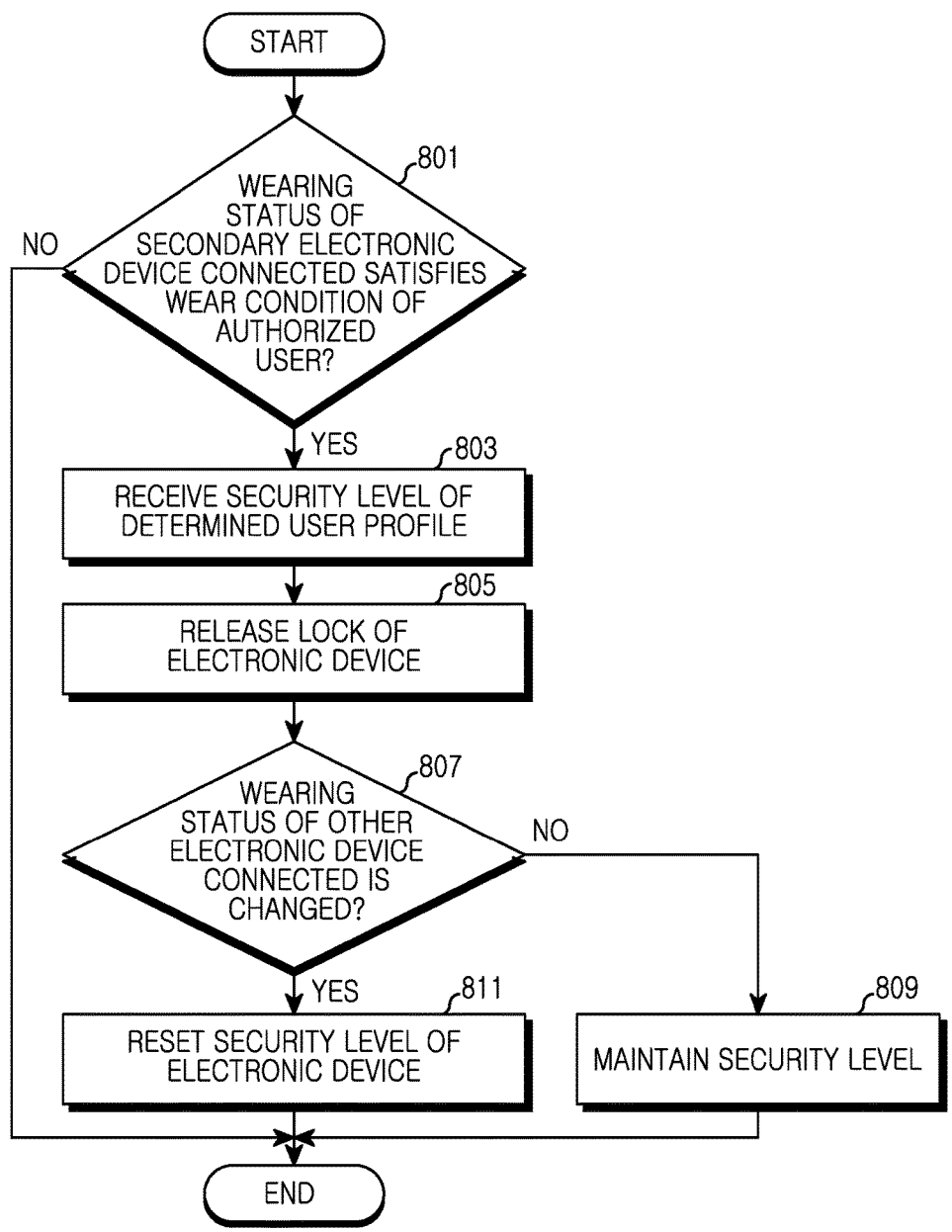
FIG. 8 is a flowchart of a security processing method of an electronic device, according to an embodiment of the present invention.

FIG. 8 is a flowchart of a security processing method of an electronic device, according to an embodiment of the present invention.

The first electronic device 101 is able to control its security level based on the wearing status information or the user profile received from the secondary electronic device 102.

In step 801, the first electronic device 101 determines whether the wearing status information obtained by the wearable secondary electronic device 102 connected via the network communication satisfies the preset condition. For example, the secondary electronic device 102 obtains its wearing status information through one or more sensors. The first electronic device 101 or the secondary electronic device 102 determines whether the obtained wearing status information satisfies one or more preset conditions for controlling the security level in the security environment of the first electronic device 101. The preset condition can be satisfied by determining the user profile meeting the obtained wearing status information among one or more user profiles recorded to the first electronic device 101 or the secondary electronic device 102. If the obtained wearing status information satisfies one or more preset conditions for controlling the security level, then the electronic device proceeds to step 803. If one or more preset conditions for controlling the security level is not satisfied, then the process ends.

In step 803, the first electronic device 101 provides an operation according to the security level of the determined user profile. The first electronic device 101 and the secondary electronic device 102 can share one or more same user profiles. When the user profile determined by the wearing status information of the secondary electronic device 102 is absent in the first electronic device 101, the secondary electronic device 102 sends, to the first electronic device 101, the security level of the determined user profile and the information for providing the security environment corresponding to the user profile via an instruction prearranged with the first electronic device 101. The first electronic device 101 confirms the user profile determined by the secondary electronic device 102. For example, the first electronic device 101 receives an identification code, such as a password or pattern, for accessing the user environment of the first electronic device 101 provided at the security level of the user profile. Alternatively, the first electronic device 101 receives information for automatically controlling the security level according to the user profile determined by the secondary electronic device 102.

In step 805, when the input identification code is correct, the first electronic device 101 changes the security level according to the granted authority of the user profile. For example, when receiving the user profile from the secondary electronic device 102, the first electronic device 101 provides the user environment at the security level according to the received user profile.

In step 807, the first electronic device 101 or the secondary electronic device 102 determines whether the wearing status of the secondary electronic device 102 is changed during the operation of the first electronic device 101 according to the authorized user profile. For example, when the connection of the sensor or the device providing the information to determine the user profile according to the preset location such as buckle (pin or hole) or tension sensor, the secondary electronic device 102 sends the change information to the first electronic device 101. Alternatively, the first electronic device 101 detects an error (e.g., disconnection) of the data transmission/reception of the network communication with the secondary electronic device 102 during its operation of the first electronic device 101 according to the granted authority of the determined security level.

When detecting a change of the wearing status information or the network communication of the secondary electronic device 102, the first electronic device 101 proceeds to step 811. Otherwise, the first electronic device 101 proceeds to step 809.

In step 811, the first electronic device 101 resets the security level. When detecting the changed wearing status of the secondary electronic device 102 at the current security level (e.g., the security level of the first electronic device 101 with the authority granted based on the identification code), the first electronic device 101 changes its security level. For example, when the secondary electronic device 102 is taken off while at a low security level according to the identification code, the first electronic device 101 changes the security level to the highest security level. When changing the security level to the highest security level, the first electronic device 101 may output the information indicating that the secondary electronic device 102 has been taken off. When the first electronic device 101 outputs the information indicating that the secondary electronic device 102 is taken off and the secondary electronic device 102 is put on again, according to the wearing status information, within a preset time, the first electronic device 101 operates under the granted authority of the user profile with the identification code input at a lower security level than the security level of the user profile determination.

When the secondary electronic device 102 is taken off or the connection of the network communication with the first electronic device 101 has an error, the first electronic device 101 releases the current user profile.

In step 809, the first electronic device 101 maintains the current security level and security environment during an operation of the authorized user. For example, when the display module 150 is turned off, the first electronic device 101 maintains the security release according to the setting which controls to change the security level of the security release (the security status of the first electronic device 101 with the granted authority) to the security level of the lock status of the corresponding user, without locking the security level.

After step 809 or 811, the process of FIG. 8 ends.

The first electronic device 101 can provide a service by applying the user profile determined based on the wearing status information of the secondary electronic device 102, and may select (or determine) the user and serve as a secondary security device for the operations, except for the user profile determination, based on the wearing status information of the secondary electronic device 102.

An operating method of a first electronic device 101 includes obtaining wearing status information of a secondary electronic device 102 which is wearable, and determining a security environment of the first electronic device based on the wearing status information.

When a user puts the secondary electronic device 102 on and then the user is determined as a preset user according to the wearing status information obtained, the first electronic device 101 may lower a security level of the security environment.

When the secondary electronic device 102 is a watch type, the wearing status information detects that a preset hole of the secondary electronic device 102 is used when a user wears the secondary electronic device 102.

The wearing status information can be determined using one or more of a fingerprint sensor, an iris sensor, a pulse wave sensor, a temperature sensor, a grip sensor, and a tension sensor, which are connected to the secondary electronic device 102.

The secondary electronic device 102 can be connected to the first electronic device 101 through one or more network communications.

The wearing status information is periodically obtained when the first electronic device 101 and the secondary electronic device 102 are connected.

The security level is included in a user profile determined based on the wearing status information.

A content range is able to be limited based on the security level, according to the security environment, by applying the security level to all or part of the content of the first electronic device 101.

The method further includes, after determining the security level, detecting a change of the received wearing status information or receiving no wearing status information. The method further includes changing the security environment of the first electronic device 101 in a preset manner and providing a content corresponding to the changed security environment.

An operating method of the first electronic device 101 includes determining a wearing status of the first electronic device 101, determining a security level or a user profile corresponding to the wearing status, and sending information of the security level or the user profile to a secondary electronic device 102. The first electronic device 101 can include one or more of a fingerprint sensor, an iris sensor, a pulse wave sensor, a temperature sensor, a grip sensor, and a tension sensor, and determines wearing status information of the first electronic device 101 using one or more of the sensors.

Figure 9:
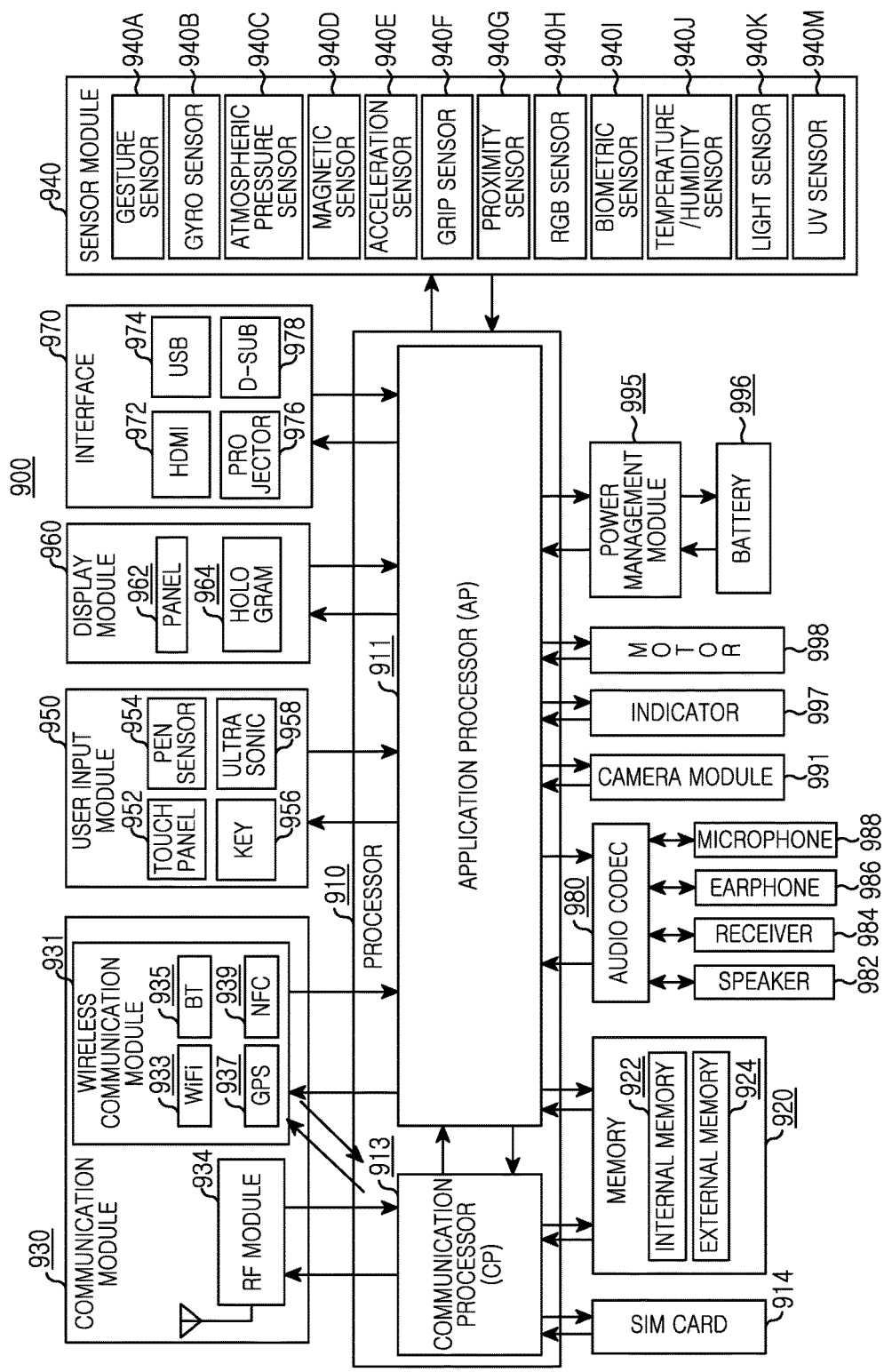
FIG. 9 is a block diagram of hardware of an electronic device, according to an embodiment of the present invention.

FIG. 9 is a block diagram of hardware of an electronic device, according to an embodiment of the present invention.

Referring to FIG. 9, the hardware 900 can configure all or part of the first electronic device 101 of FIG. 1. The hardware 900 can include one or more processors 910, a Subscriber Identity Module (SIM) card 914, a memory 920, a communication module 930, a sensor module 940, a user input module 950, a display module 960, an interface 970, an audio codec 980, a camera module 991, a power management module 995, a battery 996, an indicator 997, and a motor 998.

The processor 910 (e.g., the processor 120) can include one or more Application Processors (APs) 911 and one or more Communication Processors (CPs) 913. For example, the processor 910 can be the processor 120 of FIG. 1. While the AP 911 and the CP 913 are included in the processor 910 of FIG. 9, the AP 911 and the CP 911 can be included in different Integrated Circuit (IC) packages. The AP 911 and the CP 911 may be included in a single IC package.

The AP 911 controls a plurality of hardware or software components connected to the AP 911 by driving an operating system or an application program, and carries out data processing and operations including multimedia data. The AP 911 can be implemented using, for example, a System on Chip (SoC). The processor 910 can further include a Graphics Processing Unit (GPU).

The CP 913 manages data links and converts a communication protocol in the communication between the first electronic device 101 including the hardware 900 and the other electronic devices connected over the network. The CP 913 can be implemented using, for example, a SoC. The CP 913 performs at least part of a multimedia control function. The CP 913 identifies and authenticates a terminal in the communication network using the SIM card 914. In so doing, the CP 913 can provide the user with services including voice telephony, video telephony, text message, and packet data.

The CP 913 controls the data transmission and reception of the communication module 930. While the components of the CP 913, the power management module 995, and the memory 920 are separated from the AP 911 in FIG. 9, the AP 911 can include part (e.g., the CP 913) of those components.

The AP 911 or the CP 913 loads and processes the instruction or the data received from its non-volatile memory or at least one of the other components, in a volatile memory. The AP 911 or the CP 913 stores data received from or generated by at least one of the other components, in the non-volatile memory.

The SIM card 914 can be inserted to a slot formed at a specific location of the electronic device. The SIM card 914 can include unique identification information (e.g., Integrated Circuit Card Identifier (ICCID)) or subscriber information (e.g., International Mobile Subscriber Identity (IMSI)).

The memory 920 includes an internal memory 922 and an external memory 924. For example, the memory 920 can be the memory 130 of FIG. 1. The internal memory 922 can include at least one of the volatile memory (e.g., Dynamic Random Access Memory (DRAM), Static RAM (SRAM), Synchronous DRAM (SDRAM)) and the non-volatile memory (e.g., One-Time Programmable Read Only Memory (OTPROM), PROM, Erasable PROM (EPROM), Electrically EPROM (EEPROM), mask ROM, flash ROM, NAND flash memory, NOR flash memory). The internal memory 922 may employ a Solid State Drive (SSD). The external memory 924 can further include a flash drive, for example, a Compact Flash (CF), a Secure Digital (SD), a Micro-SD, a Mini-SD, an extreme digital (xD), and a memory stick.

The communication module 930 can include a wireless communication module 931 and a Radio Frequency (RF) module 934. For example, the communication module 930 can be the communication module 170 of FIG. 1. For example, the wireless communication module 931 can include a Wi-Fi 933, a BT 935, a GPS 937, and an NFC 939. For example, the wireless communication module 931 can provide a wireless communication function using a radio frequency. Additionally, the wireless communication module 931 can include a network interface (e.g., LAN card) or a modem for connecting the hardware 900 to the network (e.g., Internet, LAN, WAN, telecommunication network, cellular network, satellite network, or POTS).

The RF module 934 can control the data transmission and reception, for example, the transmission and reception of the RF signal or a called electric signal. For example, the RF module 934 can includes a transceiver, a Pulse Amplitude Modulation (PAM), a frequency filter, or a Low Noise Amplifier (LNA), which is not depicted in the drawing. The RF module 934 can further include a component, for example, a conductor or a conducting wire, for sending and receiving electromagnetic waves in a free space in the wireless communication.

The sensor module 940 can include at least one of, for example, a gesture sensor 940A, a gyro sensor 940B, an atmospheric pressure sensor 940C, a magnetic sensor 940D, an acceleration sensor 940E, a grip sensor 940F, a proximity sensor 940G, a Red Green Blue (RGB) sensor 940H, a biometric sensor 940I, a temperature/humidity sensor 940J, a light sensor 940K, and an UltraViolet (UV) sensor 940M. The sensor module 940 measures a physical quantity or detects the operation status of the electronic device, and converts the measured or detected information to an electric signal. Additionally, the sensor module 940 can include an E-noise sensor, an electromyography (EMG) sensor, an electroencephalogram (EEG) sensor, an electrocardiogram (ECG) sensor, or a finger print sensor. The sensor module 940 can further include a control circuit for controlling its one or more sensors.

The user input module 950 can include a touch panel 952, a (digital) pen sensor 954, a key 956, and an ultrasonic input device 958. For example, the user input module 950 can be the input/output interface module 140 of FIG. 1. The touch panel 952 can recognize the touch input using at least one of capacitive, resistive, infrared, and Surface Acoustic Wave (SAW) techniques. The touch panel 952 may further include a controller. The capacitive touch panel can recognize not only the direct touch but also the proximity. The touch panel 952 may further include a tactile layer. In this case, the touch panel 952 provides a tactile response to the user.

The (digital) pen sensor 954 can be implemented using the same or a similar method as the user's touch input, or using a separate recognition sheet. The key 956 can include, for example, a keypad or a touch key.

The ultrasonic input device 958, which obtains data by detecting microwave through a microphone 988 in the terminal, allows radio frequency identification through the pen which generates an ultrasonic signal. The hardware 900 may receive the user input from an external device (e.g., a network, a computer, or a server) connected using the communication module 930.

The display module 960 can include a panel 962 or a hologram 964. For example, the display module 960 can be the display module 150 of FIG. 1. The panel 962 can employ, for example, a Liquid Crystal Display (LCD) or an Active Matrix Organic Light Emitting Diode (AMOLED). The panel 962 can be implemented flexibly, transparently, or wearably. The panel 962 may be constructed as a single module together with the touch panel 952. The hologram 964 can present a three-dimensional image in the air using interference of light. The display module 960 can further include a control circuit for controlling the panel 962 and the hologram 964.

The interface 970 can include, for example, a High Definition Multimedia Interface (HDMI) 972, a Universal Serial Bus (USB) 974, a projector 976, and a D-sub 978. Additionally/substantially, the interface 970 can include, for example, a SD/MMC (not shown) or IrDA (not shown).

The audio codec 980 converts voice data to an electronic signal and vice versa. For example, the audio codec 980 can convert voice information which is input or output through a speaker 982, a receiver 984, an earphone 986, or the microphone 988.

The camera module 991 can capture a still picture and a moving picture. For example, the camera module 991 can include one or more image sensors (e.g., front lens or rear lens), an Image Signal Processor (ISP), or a flash LED.

The power management module 995 manages power of the hardware 900. The power management module 995 can include, for example, a Power Management IC (PMIC), a charging IC, or a battery gauge.

For example, the PMIC can be mounted in an IC or a SoC semiconductor. The charging type can be a wired type and a wireless type. The charging IC can charge the battery and prevent overvoltage or overcurrent from flowing from a charger. For example, the charging IC can include a charging IC for at least one of the wired charging type or the wireless charging type. For example, the wireless charging type includes magnetic resonance, magnetic induction, and microwave, and can further include an additional circuit such as coil loop, resonance circuit, rectifier circuit for the wireless charging.

The battery gauge can measure, for example, the remaining capacity of the battery 996 and the voltage, the current, or the temperature of the charging. The battery 996 can supply the power by generating the electricity. For example, the battery 996 can be a rechargeable battery.

The indicator 997 displays a specific status of the hardware, for example, booting state, message state, or charging state of the hardware 900 or part (e.g., the AP 911) of the hardware 900.

The motor 998 converts the electric signal to a mechanic vibration. A processor (e.g. AP 911) can control the sensor module 940.

The hardware 900 can include a processor (e.g., the GPU) for supporting mobile TV. For example, the processor for supporting the mobile TV can process media data in conformity with Digital Multimedia Broadcasting (DMB), Digital Video Broadcasting (DVB), or media flow standard. The aforementioned components of the hardware can include one or more parts, and the name of the corresponding component can differ according to the type of the electronic device. The hardware of the present invention can include at least one of the components, omit some components, or further include other components. Some of the hardware components can be united to a single entity to carry out the same functions of the corresponding components.

The first electronic device 101 includes a memory for storing one or more security environments, and one or more processors for obtaining wearing status information of the secondary electronic device 102 which is wearable, determining a security environment of the first electronic device 101 based on the wearing status information.

When a user puts the secondary electronic device 102 on and then the user is determined as a preset user according to the wearing status information obtained, the processor may lower the security level of the security environment.

When the secondary electronic device 102 is a watch type, the processor detects that the wearing status information uses a preset hole of the secondary electronic device 102 when a user wears the secondary electronic device 102.

The processor determines the wearing status information using one or more of a fingerprint sensor, an iris sensor, a pulse wave sensor, a temperature sensor, a grip sensor, and a tension sensor, which are connected to the secondary electronic device 102.

The processor receives the wearing status information through one or more network communications connecting the first electronic device 101 and the secondary electronic device 102.

The processor periodically obtains the wearing status information when the first electronic device 101 and the secondary electronic device 102 are connected.

The processor is able to limit a content range based on a security level of the security environment by applying the security level to all or part of the content of the first electronic device 101.

After determining the security environment, the processor is able to detect a change of the received wearing status information or the processor may receive no wearing status information. The processor is then able to change the security environment of the first electronic device 101 in a preset manner and provide content corresponding to the changed security environment.

After determining the security environment, when determining that there was no change of the received wearing status information, the processor maintains the security environment of the electronic device.

The secondary electronic device 102 includes a memory for storing one or more security environments, and one or more processors for determining a wearing status of the secondary electronic device 102 using one or more sensors, determining a security level or a user profile corresponding to the wearing status, and sending information of the security level or the user profile to a first electronic device, The processor determines wearing status information of the secondary electronic device using one or more of a fingerprint sensor, an iris sensor, a pulse wave sensor, a temperature sensor, a grip sensor, and a tension sensor of the secondary electronic device 102.

As set forth above, the security mode of the first electronic device 101 is able to be controlled according to the wearing status of the secondary electronic device 102 which is wearable and connected through the network communication, and a multi-security system can be established by concurrently using the security method with one or more secondary electronic devices in addition to the present security method applied to the first electronic device 101.

Various embodiments for describing the present invention may be performed by using one or more programs included in the memory 130 of the first electronic device 101, or may be directly controlled by a processor (e.g., the processor 120). In addition, the embodiments may also be controlled by using one or more control modules (e.g., the security processing module 105). And the security processing module may be controlled by the processor.

The term "module" used in various embodiments of the present invention can indicate, for example, a unit including a combination of one or more of hardware, software, or firmware. The "module" can be interchangeably used with the term, for example, a unit, logic, a logical block, a component, or a circuit. The "module" can be a minimum unit or part of the components integrally formed. The "module" may be a minimum unit or part for one or more functions. The "module" can be implemented mechanically or electronically. For example, the "module" according to various embodiments of the present invention can include at least one of an Application-Specific Integrated Circuit (ASIC) chip, Field-Programmable Gate Arrays (FPGAs), or a programmable-logic device for performing operations which are well known or to be invented.

According to various embodiments of the present invention, at least part of the device (e.g., modules or functions) or the method (e.g., operations) according to various embodiments of the present invention can be implemented as, for example, an instruction stored in a computer-readable storage media in the form of a programming module. When the instruction is executed by one or more processor (e.g., the processor 810), the one or more processors can perform a function corresponding to the instruction. The computer-readable storage medium can be, for example, the memory 860. At least part of the programming module can be implemented by the processor 810. At least part of the programming module can include, for example, a module, a program, sets of instructions, or a process for performing one or more functions.

The programming module according to various embodiments of the present invention can include at least one of the aforementioned components, omit some components, or further include other components. The operations fulfilled by the programming modules or other components according to various embodiments of the present invention can be carried out in sequence, in parallel, repeatedly, or heuristically. Also, some operations can be executed in a different order or omitted, or other operations can be added.

The computer-readable recording medium can include magnetic media such as hard disk, floppy disk and magnetic tape, optical media such as Compact Disc Read Only Memory (CD-ROM) and Digital Versatile Disc (DVD), magneto-optical media such as floptical disk, and hardware devices specifically configured to store and execute the application instruction (e.g., the programming module) such as Read Only Memory (ROM), Random Access Memory (RAM), and flash memory. Also, the application instruction can include not only a machine code made by a complier but also a high-level language code executable by a computer using an interpreter. The above-stated hardware device can serve as one or more software modules for fulfilling the operations of various embodiments of the present invention, and vice versa.

While the invention has been shown and described with reference to certain embodiments thereof, it will be understood by those skilled in the art that various changes in form and details may be made therein without departing from the spirit and scope of the invention as defined by the appended claims and their equivalents.

What is claimed is:

1. A portable electronic device comprising:
    a display;
    a communication interface configured to communicate with a wearable device using wireless short-range communication; and
    a processor configured to:
        establish a connection between the portable electronic device and the wearable device;
        receive, via the communication interface, a security status of the connected wearable device from the connected wearable device;
        limit access to at least one setting item among a plurality of setting items included in an application, in response to the security status corresponding to a lock status, the at least one setting item being predefined among the plurality of setting items and relating to a passcode; and
        allow access to the at least one setting item, in response to the security status corresponding to an unlock status.

2. The portable electronic device of claim 1, wherein the wearable device is a wrist watch having a pulse sensor positioned on a back side of a body of the wrist watch, the pulse sensor being used to determine a wearing status of the wrist watch, and
    wherein the security status of the wrist watch is changed from the unlock status to the lock status in response to no wearing status information.

3. The portable electronic device of claim 1, wherein the processor is further configured to provide, via the display, a menu for inputting password data of the portable electronic device.

4. The portable electronic device of claim 1, wherein the processor is further configured to detect disconnection of the wireless short-range communication while access to the at least one setting item is allowed, and to limit access to the at least one setting item, in response to the detection of the disconnection of the wireless short-range communication.

5. The portable electronic device of claim 1, wherein the processor is further configured to periodically receive the security status from the wearable device.

6. The portable electronic device of claim 1, wherein a wearing status of the wearable device is detected by a sensor affixed to the wearable device, and the security status is determined based on the detected wearing status.

7. The portable electronic device of claim 6, wherein the wearable device is a wrist watch, and the sensor is a pulse sensor that detects a pulse rate.

8. The portable electronic device of claim 6, wherein, when a user wears the wearable device, the sensor is positioned adjacent to the user's wrist.

9. A method for controlling a portable electronic device, the method comprising:
    establishing a connection between the portable electronic device and a wearable device;
    receiving a security status of the connected wearable device from the connected wearable device;
    limiting access to at least one setting item among a plurality of setting items included in an application, in response to the security status being a lock status, the at least one setting item being predefined among the plurality of setting items and relating to a passcode; and
    allowing access to the at least one setting item, in response to the security status being an unlock status.

10. The method of claim 9, further comprising:
    changing from the unlock status to the lock status in response to a determination that the wearable device is not being worn,
    wherein the wearable device is a wrist watch having a pulse sensor positioned on a back side of a body of the wrist watch,
    wherein the pulse sensor determines a wearing status of the wrist watch, and
    wherein the security status is changed from the unlock status to the lock status in response to a change in the wearing status indicating that the wrist watch is not being worn.

11. The method of claim 9, further comprising providing a menu for inputting password data of the portable electronic device.

* * * * *